US00PP22992P2

(12) United States Plant Patent
Snijders

(10) Patent No.: US PP22,992 P2
(45) Date of Patent: Aug. 28, 2012

(54) ***IMPATIENS* PLANT NAMED 'BALCOREE'**

(50) Latin Name: *Impatiens walleriana*
Varietal Denomination: Balcoree

(75) Inventor: Charles Snijders, Lunteren (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 13/134,197

(22) Filed: Jun. 1, 2011

(51) Int. Cl.
*A01H 5/00* (2006.01)

(52) U.S. Cl. ..... Plt./317

(58) Field of Classification Search ..... Plt./317
See application file for complete search history.

*Primary Examiner* — Kent L Bell
(74) *Attorney, Agent, or Firm* — Audrey Charles

(57) ABSTRACT

A new and distinct cultivar of *Impatiens* plant named 'Balcoree', characterized by its double-type, deep salmon-rose colored flowers, dark green-colored foliage, and moderately vigorous, compact-mounded growth habit, is disclosed.

1 Drawing Sheet

Latin name of genus and species of plant claimed: *Impatiens walleriana.*

Variety denomination: 'Balcoree'.

BACKGROUND OF THE INVENTION

The present invention relates to a new and distinct cultivar of *Impatiens* plant botanically known as *Impatiens walleriana* and hereinafter referred to by the cultivar name 'Balcoree'.

The new cultivar originated in a controlled breeding program in Rijsenhout, The Netherlands during February 2007. The objective of the breeding program was the development of *Impatiens* cultivars with fully double-type flowers, attractive flower and foliage coloration, and a freely branching, compact-mounded growth habit.

The new *Impatiens* cultivar is the result of cross-pollination. The female (seed) parent of the new cultivar is the proprietary *Impatiens walleriana* breeding selection designated 5132c-5, not patented, characterized by its semi-double type, dark red-colored flowers, dark green-colored foliage, and moderately vigorous, compact growth habit. The male (pollen) parent of the new cultivar is the proprietary *Impatiens walleriana* breeding selection designated 5281-5, not patented, characterized by its double-type, red and white bicolored flowers, dark bronze green-colored foliage, and moderately vigorous, mounded growth habit. The new cultivar was discovered and selected as a single flowering plant within the progeny of the above stated cross-pollination during July 2007 in a controlled environment in Rijsenhout, The Netherlands.

Asexual reproduction of the new cultivar by terminal stem cuttings since July 2007 at Rijsenhout, The Netherlands and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcoree' as a new and distinct cultivar of *Impatiens* plant:

1. Double-type, deep salmon-rose colored flowers;
2. Dark green-colored foliage; and
3. Moderately vigorous, compact-mounded growth habit.

Plants of the new cultivar differ from plants of the female parent primarily in flower type and flower color and from plants of the male parent primarily in flower color and foliage color.

Of the many commercially available *Impatiens* cultivars, the most similar in comparison to the new cultivar is 'Musica Pastel Salmon', not patented. However, in side by side comparisons, plants of the new cultivar differ from plants of 'Musica Pastel Salmon' in at least the following characteristics:

1. Plants of the new cultivar have a flower color different from plants of 'Musica Pastel Salmon';
2. Plants of the new cultivar have more inflorescences per plant than plants of 'Musica Pastel Salmon'; and
3. Plants of the new cultivar are larger, as measured by plant height and width, than plants of 'Musica Pastel Salmon'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcoree'. The plants were grown in 4-inch pots for 8 weeks in a greenhouse at West Chicago, Ill.

DETAILED BOTANICAL DESCRIPTION

Figure 1:
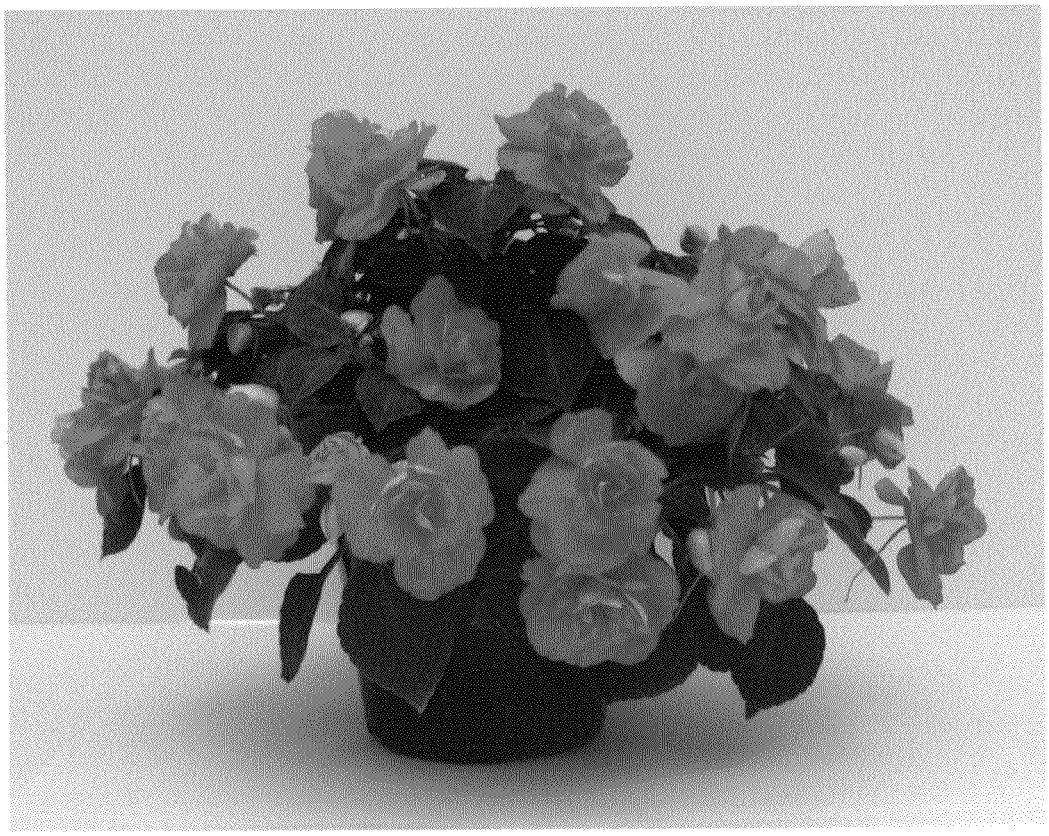
FIG. 1 illustrates a side view of the overall growth and flowering habit of 'Balcoree'.
Figure 2:
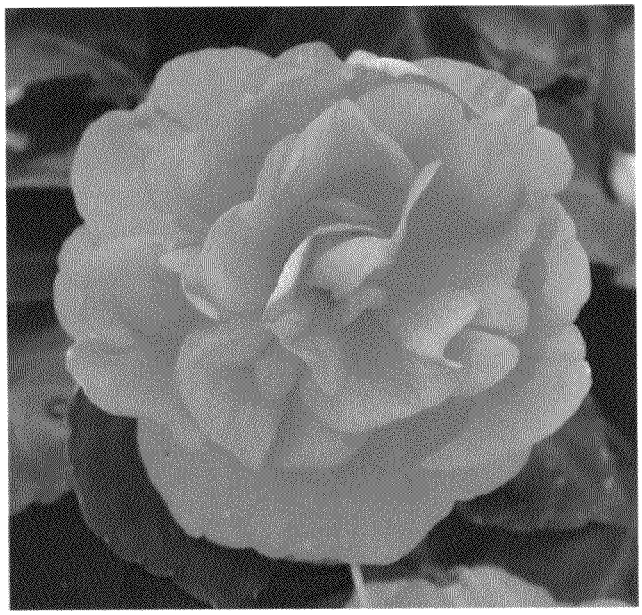
FIG. 2 illustrates a close-up view of an individual flower of 'Balcoree'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in March 2011 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 8 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Impatiens walleriana* cultivar Balcoree.

Parentage:

*Female parent*.—Proprietary *Impatiens walleriana* breeding selection designated 5132c-5, not patented.

*Male parent*.—Proprietary *Impatiens walleriana* breeding selection designated 5281-5, not patented.

Propagation:

*Type cutting*.—Terminal stem.

*Time to initiate roots*.—Approximately 7 to 8 days.

*Time to produce a rooted cutting*.—Approximately 21 to 24 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Moderately vigorous, compact-mounded growth habit.

*Size*.—Height from soil level to top of plant plane: Approximately 12.8 cm. Width: Approximately 24.4 cm.

*Branching habit*.—Freely branching. Quantity of main branches per plant: Approximately 8.

*Branch*.—Strength: Moderately strong. Length: Approximately 9.9 cm. Diameter at central internode: Approximately 4.0 mm. Length of central internode: Approximately 1.9 cm. Texture: Glabrous. Color of young and mature stems: 147C with streaks of 187B at the node regions.

Foliage description:

*General description*.—Quantity of leaves per main branch: Approximately 9. Fragrance: None. Form: Simple. Arrangement: Alternate.

*Leaves*.—Aspect: Acute angle to stem, becoming perpendicular with age. Shape: Ovate. Margin: Crenate, ciliate. Apex: Acute. Base: Attenuate. Venation pattern: Pinnate. Length of mature leaf at center of stem: Approximately 3.6 cm. Width of mature leaf at center of stem: Approximately 3.0 cm. Texture of upper and lower surfaces: Glabrous. Color of upper surface of young foliage: 137A with venation of 137C. Color of lower surface of young and mature foliage: 191B with patches of 187B with venation of 138A. Color of upper surface of mature foliage: Slightly darker than 137A with venation of 137C.

*Petiole*.—Length: Approximately 2.3 cm. Diameter: Approximately 2.0 mm. Texture: Glabrous. Color: 147D to 147C with streaks of 187B.

Flowering description:

*Flowering habit*.—'Balcoree' is freely flowering under outdoor growing conditions with substantially continuous blooming from spring through autumn and year-round in greenhouse environment.

*Lastingness of individual flower on the plant*.—Approximately 7 to 8 days.

Flower description:

*General description*.—Type: Double. Quantity per plant: Approximately 22. Fragrance: None.

*Bud*.—Rate of opening: Generally takes 2 to 3 days for bud to progress from first color to fully open flower. Quantity showing color per plant: Approximately 6.

*Bud just before opening*.—Shape: Ovoid. Length: Approximately 1.5 cm. Diameter: Approximately 1.1 cm. Color: 58D.

*Corolla*.—Shape: Hemispherical. Width: Approximately 4.8 cm. Depth: Approximately 2.4 cm. Borne: Above the foliage.

*Petals*.—Quantity: 28. Shape: Obovate; innermost are irregular. Aspect: Flat. Appearance: Iridescent. Margin: Entire. Apex: Obtuse; some are emarginate. Base: Attenuate. Length of outermost petals: Approximately 2.4 cm. Width of outermost petals: Approximately 2.1 cm. Length of innermost petals: Approximately 1.2 cm. Width of innermost petals: Approximately 7.0 mm. Texture of upper and lower surfaces: Glabrous. Color of upper surface when first and fully open: 47C occasionally with an overlay of 72C. Color of lower surface when first and fully open: Closest to but lighter than 47D.

*Spur*.—Quantity: 1 per flower. Length: Approximately 3.3 cm. Diameter at proximal end: Approximately 1.0 mm. Diameter at distal end: Less than 1 mm. Texture: Glabrous. Color: 147D with an overlay of 187B.

*Peduncle*.—Strength: Moderately strong. Aspect: Acute angle to stem. Length: Approximately 2.4 cm. Diameter: Approximately 2.0 mm. Texture: Glabrous. Color: 147C with an overlay of 187B.

*Sepals*.—Quantity per flower: 4 with one fused to base of upper petal. Sepal arrangement: 1 spurred lower sepal located between 2 side (lateral) sepals. Shape of lateral sepals: Lanceolate. Shape of lower sepal: Ovate. Apex of all sepals: Acute. Length of lateral sepals: Approximately 3.0 mm. Width of lateral sepals: Approximately 1.0 mm. Length of lower sepal: Approximately 1.5 cm. Width of lower sepal: Approximately 1.0 cm. Texture of upper surface of all sepals: Glabrous. Texture of lower surface of all sepals: Glabrous. Color of upper and lower surfaces of lateral sepals: 144A. Color of upper and lower surfaces of lower sepal: N155B with 145B at tip.

*Reproductive organs*.—None observed.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balcoree', substantially as herein shown and described.

* * * * *